(12) United States Patent
Wershofen et al.

(10) Patent No.: US 8,450,516 B2
(45) Date of Patent: May 28, 2013

(54) CATALYST FOR PRODUCING N-SUBSTITUTED CARBAMATES, AND THE PREPARATION AND APPLICATION OF THE SAME

(75) Inventors: Stefan Wershofen, Mönchengladbach (DE); Stephan Klein, Shanghai (CN); Hongchao Li, Pudong (CN); Xinkui Wang, Shanxi (CN); Qifeng Li, Shanxi (CN); Maoqing Kang, Shanxi (CN)

(73) Assignee: Bayer MaterialScience AG, Leverkusen (DE)

( * ) Notice: Subject to any disclaimer, the term of this patent is extended or adjusted under 35 U.S.C. 154(b) by 447 days.

(21) Appl. No.: 12/780,994

(22) Filed: May 17, 2010

(65) Prior Publication Data

US 2010/0298592 A1 Nov. 25, 2010

(30) Foreign Application Priority Data

May 19, 2009 (CN) .......................... 2009 1 0051496

(51) Int. Cl.
*C07C 261/00* (2006.01)
(52) U.S. Cl.
USPC ....................................................... 560/24
(58) Field of Classification Search
None
See application file for complete search history.

(56) References Cited

U.S. PATENT DOCUMENTS

| 3,763,217 A | 10/1973 | Brill |
| 4,268,683 A | 5/1981 | Gurgiolo |
| 4,381,403 A | 4/1983 | Falcone et al. |
| 4,388,238 A | 6/1983 | Heitkämper et al. |

OTHER PUBLICATIONS

Database CAPLUS Chemical Abstracts Service, Columbus, Ohio, US; Database Accession No. 2010:225211, Abstract of Gharib et al.; International Electronic Conference on Synthetic Organic Chemistry, 13th, Nov. 1-30, 2009, ghari1/1-ghari1/8. Editor(s): Seijas, Julio A.; Vazquez Tato, M. Pilar. Publisher: Molecular Diversity Preservation Internat.*

* cited by examiner

*Primary Examiner* — Karl J Puttlitz
(74) *Attorney, Agent, or Firm* — N. Denise Brown

(57) ABSTRACT

The present invention relates to a novel catalyst for producing N-substituted carbamates, the preparation of the catalyst and an improved method for producing N-substituted carbamates from these novel catalysts. The active component of the catalyst is a heteropoly acid and the catalyst support comprises a metal oxide or a metalloid oxide. The catalyst can be used to promote the reaction of carbamate and amine, thereby generating N-substituted carbamates with high yield. In the presence of the catalyst, the reaction conditions are relatively mild, the catalytic activity and selectivity of the reaction are high, and the reaction time is relatively short. Furthermore, the catalyst can be conveniently separated from the reaction system and recycled. therefore, the catalyst can be used to facilitate the further scale-up test and commercial application.

11 Claims, No Drawings

CATALYST FOR PRODUCING N-SUBSTITUTED CARBAMATES, AND THE PREPARATION AND APPLICATION OF THE SAME

CROSS-REFERENCE TO RELATED PATENT APPLICATION

The present patent application claims the right of priority under 35 U.S.C. §119 (a)-(d) of Chinese Patent Application No. 200910051496.4, filed May 19, 2009.

BACKGROUND OF THE INVENTION

The present invention relates to N-substituted carbamates, and particularly to a catalyst for preparing these N-substituted carbamates. This invention also relates to the novel catalyst, to the preparation of the catalyst, and to the use thereof.

N-substituted carbamates represent a class of important organic intermediates, which can be used for the manufacture of agrochemicals, dyes, pharmaceuticals, ureas, and isocyanates. Furthermore, they can also be applied as protective groups of amides in various organic syntheses.

The synthesis of N-substituted carbamates has received considerable attention due to their wide applications. For example, U.S. Pat. No. 3,763,217 and U.S. Pat. No. 4,268,683 disclose the synthesis of N-substituted carbamates by reacting aromatic amines with organic carbonates in the presence of $AlCl_3$, $FeCl_3$, $UO_2(NO)_2$, zinc acetate, zinc propionate, or zinc naphthenate as a catalyst, respectively. This method has low selectivity for the desired products. Moreover, the catalyst activity is restricted by the aromatic amines. Both DE 2943480 and U.S. Pat. No. 4,381,403 disclose that homogeneous $ZnCl_2$ or tertiary amine can be used as a catalyst in the synthesis of N-substituted carbamates by reacting carbamates and amines. However, these catalysts are difficult to separate and recover from the reaction mixtures. Thus, these catalyst can not be conveniently recycled.

From the perspective of commercial application, it is necessary to develop a new catalyst for preparing N-substituted carbamates. The catalyst should not only be capable of preparing the targeted products in high yields, but should also be convenient to separate from the product and recycled.

SUMMARY OF THE INVENTION

One aspect of the present invention is to provide a method for preparing N-substituted carbamates. In accordance with the present invention, this method comprises reacting a carbamate with an amine in the presence of a catalyst to form an N-substituted carbamate, wherein the catalyst comprises a heteropoly acid as active component and a metal oxide or a metalloid oxide as catalyst support.

Another aspect of the present invention is to provide a novel catalyst which is suitable for preparing N-substituted carbamates. In accordance with the present invention, the catalyst comprises an active component and a catalyst support component. The active component of the catalyst is a heteropoly acid, and the component of the catalyst support is a metal oxide or a metalloid oxide.

The third aspect of the present invention is to provide a method for preparing this catalyst. According to the present invention, the method comprises (1) impregnating a catalyst support into a heteropoly acid solution comprising one or more heteropoly acids to form a catalyst precursor, and (2) calcinating the catalyst precursor to obtain a catalyst, wherein the calcination temperature ranges from 150 to 1000° C.

In accordance with the present invention, N-substituted carbamates can be prepared with high yield by reacting N-unsubstituted carbamates with amines in the presence of the catalyst provided here. The reaction system can be easily scaled up, due to the fact that the reaction conditions are relatively mild, and the activity and selectivity of the catalyst are high, and the reaction time is rather short. Furthermore, the catalyst can be easily separated from the reaction system and recycled.

DETAILED DESCRIPTION OF THE INVENTION

Heteropoly acids (HPAs) are commonly regarded as attractive catalytic materials and are applied to a variety of reactions such as, for example, dehydration, cyclization, esterification, and so on. However, homogeneous HPAs are difficult to separate and recover from the reaction mixture. Therefore, HPAs can not be conveniently recycled.

The present invention provides a new catalyst comprising an active component and a catalyst support component, with the active component comprising a heteropoly acid, and the catalyst support component comprising a metal oxide or a metalloid oxide. It has been found that in the presence of such catalyst, carbamates react with amines to form N-substituted carbamates in high yield. In addition, the catalyst can be separated from the reaction system and recycled easily. This makes commercial scale-up and application commercially feasible.

A preferred embodiment of the catalyst is hat the catalyst support component comprises vanadium pentoxide ($V_2O_5$). It has been found that there is a synergistic action between $V_2O_5$ as the catalyst support component, and Keggin type HPAs as the active component of the catalyst, which further enhance the selectivity and increase the yield of the reaction.

Catalyst for Preparing N-Substituted Carbamates

The active component of the catalyst of the present invention is a Heteropoly acid (HPAs), preferably a Keggin type Heteropoly acids (HPAs). More preferred Keggin type Heteropoly acids include tungstophoric acid ($H_3PW_{12}O_{40}.nH_2O$), molybdophosphoric acid ($H_3PMo_{12}O_{40}.nH_2O$), tungstosilicic acid ($H_4SiW_{12}O_{40}.nH_2O$), molybdosilicic acid ($H_4SiMo_{12}O_{40}.nH_2O$), or their mixtures. It is most preferred that the Keggin type Heteropoly acid be selected from the group consisting of tungstophosphoric acid ($H_3PW_{12}O_{40}.nH_2O$), molybdophosphoric acid ($H_3PMo_{12}O_{40}.nH_2O$) and mixtures thereof.

The catalyst of this invention also requires a catalyst support component. This catalyst support component is a metal oxide or a metalloid oxide. Preferably, the metal oxide or metalloid oxide is selected from the group consisting of zirconia, titania, zinc oxide, silica, magnesia, calcium oxide, stannic oxide, barium oxide, cerium oxide, lanthanum oxide, vanadium pentoxide, alumina and mixtures thereof. More preferably, the catalyst support component is selected from the group consisting of vanadium pentoxide, alumina and mixtures thereof. Vanadium pentoxide is a most preferred catalyst support component.

The average diameter of the catalyst support is preferably (but not limited to) 0.1 to 4 mm, more preferably 0.5 to 3 mm, and most preferably 1 to 2 mm.

The pore volume of the catalyst support is preferably (but not limited to) 0.01 to 10 $cm^3/g$, more preferably 0.1 to 1 $cm^3/g$, most preferably 0.2 to 0.8 $cm^3/g$, and most particularly preferably 0.4 to 0.6 $cm^3/g$.

The BET surface area of the catalyst support is preferably (but not limited to) less than or equal to 300 $m^2/g$, more preferably from 1 to 250 m²/g, most preferably from 5 to 100 m²/g, and most particularly preferably from 10 to 60 m²/g.

There are no special limitations with regard to the shape of the catalyst. For example, the shape of the catalyst can be spherical, cylindrical or irregular.

The loading of the active component can be preferably (but is not limited to) from 0.1 to 20% by weight, more preferably from 1 to 10% by weight, and most preferably from 4 to 7% by weight, based on 100% by weight of the catalyst support.

Preparation of the Catalyst:

The method for preparing the catalyst comprises the steps of impregnating and calcinating, etc. The method can additionally include a drying step for the catalyst precursor after the impregnating step and before the calcinating step. The temperature of the drying step can be from (but is not limited to) less than or equal to 140° C., and more preferably from 90 to 120° C. The time of the drying step can be, but is not limited to, less than or equal to 24 hours, more preferably less than or equal to 15 hours, and most preferably from 5 to 12 hours. There is no special limitation with regard to the pressure in the drying step, however, drying preferably occurs at 1 atm. The atmosphere of the drying step can be selected from (but is not limited to) preferably air, oxygen, nitrogen, etc. More preferably the atmosphere of the drying step is air and/or oxygen, and is most preferably air.

In the impregnating step, one heteropoly acid or a mixture of two or more heteropoly acids is dissolved in a solvent to form a heteropoly acid solution. The heteropoly acid can be selected from (hut is not limited to) preferably tungstophosphoric acid ($H_3PW_{12}O_{40} \cdot nH_2O$), molybdophosphoric acid ($H_3PMo_{12}O_{40} \cdot nH_2O$), tungstosilicic acid ($H_4SiW_{12}O_{40} \cdot nH_2O$), molybdosilicic acid ($H_4SiMo_{12}O_{40} \cdot nH_2O$), or their mixtures; and most preferably tungstophosphoric acid ($H_3PW_{12}O_{40} \cdot nH_2O$), molybdophosphoric acid ($H_3PMo_{12}O_{40} \cdot nH_2O$), or their mixtures. The solvent can be selected from, but is not limited to, water, an aqueous solvent, a non-aqueous solvent, or any mixture of the aforementioned solvents. Suitable non-aqueous solvent can be selected from, preferably, ethers, alcohols, ketones, nitrites or amides; more preferably, diethyl ether, methanol, ethanol, propanol, butyl alcohol, acetone, butanone, acetonitrile, dimethyl sulfone, dimethyl sulfoxide or dimethylformamide.

The pH value of the aqueous solution comprising the precursor of the catalytically active component can be adjusted through the addition of hydrated or non-hydrated acids. The hydrated or non-hydrated acids can be selected from, but are not limited to, HCl, $HNO_3$, $H_2SO_4$, $H_3PO_4$ or $CH_3COOH$.

The catalyst precursor is obtained by impregnating a catalyst support into a solution containing the heteropoly acids. The component of the catalyst support is a metal oxide or a metalloid oxide. The metal oxide or metalloid oxide acids can be selected from, but is not limited to, preferably zirconia, titania, zinc oxide, silica, magnesia, calcium oxide, stannic oxide, barium oxide, cerium oxide, lanthanum oxide, vanadium pentoxide, alumina, or their mixtures. More preferably, the metal oxide or metalloid oxide acids are selected from vanadium pentoxide, alumina, or their mixtures. Vanadium pentoxide is the most preferred metal oxide or metalloid oxide acid.

There is no special limitation with regard to the temperature of the impregnating step. Preferably impregnating occurs at room temperature. The time of the impregnating step is typically less than or equal to 20 hours, and preferably from 1 to 4 hours.

In the calcination step, the calcination temperature should be high enough to result in the transformation of the catalyst precursor to the catalyst. The calcination temperature can be from preferably 200 to 1000° C., more preferably from 300 to 700° C. There is no special limitations with regard to the calcination time. Preferably the time ranges from 1 to 20 hours, and more preferably from 2 to 10 hours. The calcination step can be carried out either in an inert atmosphere or in an oxidizing atmosphere. The inert atmosphere can be selected from preferably (but is not limited to) a nitrogen gas, a noble gas, a non-oxidizing gas, a non-reducing gas or a mixture of two or more of the aforesaid gases. Nitrogen is more preferred as the inert gas. The oxidizing atmosphere can be selected from preferably (but is not limited to) oxygen gas or an oxygen containing gas, and more preferably is an oxygen containing gas. The oxidizing atmosphere is most preferably air. A mixture of air and nitrogen can be applied as well.

Preparation of N-Substituted Carbamates (R'(NH—CO—OR)$_n$) in the Presence of said Catalyst:

One aspect of the present invention provides a method for preparing N-substituted carbamates which correspond to the general formula:

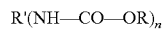

R'(NH—CO—OR)$_n$

This process comprises (1) reacting (a) one or more N-unsubstituted carbamates ($H_2N$—CO—OR), with (b) one or more amines, in the presence of (c) the novel catalyst described herein. The reaction equation is:

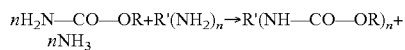

$nH_2N$—CO—OR+R'($NH_2$)$_n$→R'(NH—CO—OR)$_n$+ $nNH_3$

The N-unsubstituted carbamates ($H_2N$—CO—OR) can be obtained via known synthetic routes such as the reaction between urea and corresponding compound containing a hydroxyl group.

For the N-unsubstituted carbamates ($H_2N$—CO—OR), R can be selected from preferably, but is not limited to,
  a) a branched or unbranched, substituted or unsubstituted aliphatic group, which optionally contains one or more atoms different from C and H;
  b) a branched or unbranched, substituted or unsubstituted cycloaliphatic group, which optionally contains one or more atoms different from C and H;
  c) a branched or unbranched, substituted or unsubstituted araliphatic group, which optionally contains one or more atoms different from C and H;
  or
  d) a substituted or unsubstituted aromatic group, which optionally contains one or more atoms different from C and H.

In accordance with the above description, the atoms which are different from C (carbon) and H (hydrogen) can preferably be selected from the group consisting of, preferably, N, O, S, P, Si, F, Cl, Br and I.

The branched or unbranched, substituted or unsubstituted aliphatic group which optionally contains one or more atoms different from C and H can preferably be selected from, for example, methyl, ethyl, 1-propyl, 2-propyl, 1-butyl, 2-butyl, tert-butyl, pentyl and its isomers, hexyl and its isomers, 2-methoxy-1-ethyl, 2-ethoxy-1-ethyl, 2-hydroxy-1-ethyl, 1-hydroxy-2-propyl, 2-hydroxy-1-propyl, 4-hydroxy-1-butyl, their higher homologues or their isomers, their corresponding halogenated groups. The halogenated groups can be selected from preferably, for example, 2,2,2-triflouroethyl and 1,1,1,3,3,3-hexafluoro-2-propyl.

The branched or unbranched, substituted or unsubstituted cycloaliphatic group which optionally contains one or more atoms different from C and H can preferably be selected from, for example, but is not limited to, cyclopentyl and cyclohexyl.

The branched or unbranched, substituted or unsubstituted araliphatic group which optionally contains one or more atoms different from C and H can preferably be selected from, for example, but is not limited to, benzyl, 1-phenyl ethyl and 2-phenyl ethyl.

The substituted or unsubstituted aromatic group which optionally contains one or more atoms different from C and H can preferably be selected from, for example, but is not limited to, phenyl, hydroxyphenyl or its isomers, methoxyphenyl or its isomers, methylphenyl or its isomers, nitrophenyl or its isomers, chlorophenyl or its isomers, fluorophenyl or its isomers, bromophenyl or its isomers, iodophenyl or its isomers.

Suitable amines to be used in forming the N-substituted carbamates can be selected from, for example, but are not limited to, primary amines and secondary amines. Primary amines are preferred.

The primary amines can be characterized by the general formula:

$$R'(NH_2)_n,$$

wherein:
n is 1, 2, or any integer more than 2;
R' can be selected from the following groups.

In accordance with the present invention, R is selected from the groups:
a) a branched or unbranched, substituted or unsubstituted aliphatic group which optionally contains one or more atoms different from C and H;
b) a branched or unbranched, substituted or unsubstituted cycloaliphatic group which optionally contains one or more atoms different from C and H;
c) a branched or unbranched, substituted or unsubstituted araliphatic group which optionally contains one or more atoms different from C and H; and
d) a substituted or unsubstituted aromatic group which optionally contains one or more atoms different from C and H.

The above described R groups are not intended to be limiting.

The branched or unbranched, substituted or unsubstituted aliphatic primary amines which optionally contain one or more atoms different from C and H can preferably be selected from, for example, but are not limited to, methylamine, ethylamine, propylamine or its isomers, butylamine or its isomers, pentylamine or its isomers as well as their higher homologues, ethylene diamine, 1,2-diaminopropane, α,ω-diaminoalkanes or its isomers, substituted α,ω-diaminoalkanes or its isomers. The α,ω-diaminoalkanes can be selected from preferably, but are not limited to, 1,3-diaminopropane, 1,4-diaminobutane, 1,5-diaminopentane and 1,6 diaminohexane.

The branched or unbranched, substituted or unsubstituted cycloaliphatic primary amines which optionally contains one or more atoms different from C and H can preferably be selected from, for example, but are not limited to, cyclohexylamine, cyclohexylamines with substituted cycloaliphatic ring, diaminocyclohexane or its isomers, diaminocyclohexanes with substituted cycloaliphatic ring, isophorone diamine, 4,4'-diamino dicyclohexylmethane or its isomers, 2,4'-diamino dicyclohexylmethane or its isomers, 2,2'-diamino dicyclohexylmethane or its isomers.

The branched or unbranched, substituted or unsubstituted araliphatic primary amines which optionally contains one or more atoms different from C and H can preferably be selected from, for example, but are not limited to, benzylamine, 2-phenylethylamine, 1-phenylethylamine, o-xylylene diamine, m-xylylene diamine, p-xylylene diamine.

The substituted or unsubstituted aromatic primary amines which optionally contains one or more atoms different from C and H can preferably be selected from, for example, but are not limited to, aniline, methoxyaniline or its isomers, toluidine or its isomers, nitroaniline or its isomers, fluoroaniline or its isomers, chloroaniline or its isomers, bromoaniline or its isomers, iodoaniline or its isomers, o-phenylene diamine, m-phenylene diamine, p-phenylene diamine, aromatic ring substituted phenylene diamines, diaminotoluenes or its isomers, diamino diphenylmethane or its isomers or homologues, naphthalene diamines or its isomers. The aromatic ring substituted phenylene diamines can preferably be selected from, for example, but are not limited to, tetramethyl phenylene diamine. The diaminotoluenes or its isomers can preferably be selected from, for example, but are not limited to, 2,4-diaminotoluene or 2,6-diaminotoluene. The isomer of diamino diphenylmethane can preferably be selected from, for example, but is not limited to, 4,4'-diamino diphenylmethane, 2,4'-diamino diphenylmethane and 2,2'-diamino diphenylmethane. The isomer of naphthalene diamines can preferably be selected from, for example, but is not limited to, 1,4-naphthaline diamine, 1,5-naphthaline diamine and 1,8-naphthaline diamine.

The substituted or unsubstituted aromatic primary amines which optionally contains one or more atoms different from C and H can also include a mixture of amines obtained by the condensation reaction of aniline and formaldehyde, and the mixture comprises diamino diphenylmethane or its isomers, polyfunctional amines of the diphenylmethane series or its isomers or their higher homologues.

In the present invention, the reaction can be run by using a single amine, or a mixture of two or more of the aforementioned amines.

In the present invention, the amounts of the raw materials can be employed in such way that: at least 1 mole of carbamate ($H_2N$—CO—OR) is employed for each mole of amino groups coming from the primary amine $R'(—NH_2)_n$; preferably from 1 to 30 moles of carbamate ($H_2N$—CO—OR) are employed for each mole of amino groups coming from the primary amine $R'(—NH_2)_n$; more preferably from 1- to 15 moles of carbamate ($H_2N$—CO—OR) are employed for each mole of amino groups coming from the primary amine $R'(—NH_2)_n$; and most preferably from 4 to 10 moles of carbamate ($H_2N$—CO—OR) are employed for each mole of amino groups coming from the primary amine $R'(—NH_2)_n$.

In the present invention, the process can be run either with or without an additional solvent. In the latter case, the excess of carbamate ($H_2N$—CO—OR) serves as solvent.

When the reaction is conducted in the presence of additional solvent, the additional solvent can be a single solvent or a mixture of two or more solvents. The additional solvent can preferably be selected from, for example, but is not limited to, aliphatic or aromatic hydrocarbons or their halogenated derivatives, polar solvents, and R—OH solvents. The aliphatic or aromatic hydrocarbons or their halogenated derivatives can preferably be selected from, for example, but are not limited to, benzene, toluene, xylene or its isomers, ethylbenzene, chlorobenzene, dichlorobenzene or its isomers. The polar solvents can preferably be selected from, for example, but are not limited to, acetone, butanone, dimethylformamide, dimethyl sulfone, dimethyl sulfoxide, 1-octyl-3-methylimidazolium tetrafluoroborate ([C8-mim]$BF_4$), 1-butyl-3-methylimidazolium tetrafluoroborate ([C4-mim]$BF_4$), 1-butyl-3-methyl-imidazolium tetrafluorophosphate ([bmim]$BF_4$) or 1-butyl-3-methylimidazolium hexafluorophosphate ([bmim]$BF_6$). The R—OH solvents having the same R group as in the carbamates ($H_2N$—CO—OR) as reactant not only can facilitate the reaction, but also can depress side-reactions and enhance product selectivity. In the course of the process, a variety of intermediates and/or byproducts can be formed, e.g. substituted ureas based on the primary amines. The byproducts can be converted partially or completely to carbamates by alcoholysis with the hydroxyl component of R—OH. Generally, the molar ratio between hydroxyl groups originating from the R—OH and amino groups originating from the primary amine can preferably be selected from, for example, but is not limited to, 1 to 100, more preferably 1 to 50, most preferably 1 to 10, and most particularly preferably 2 to 8.

The amount of catalyst employed is not critical, but shall be sufficient to provide appropriate reaction rates. Preferably, the amount of catalyst applied can preferably be selected from, for example, but is not limited to, 20 parts by weight, more preferably from 0.1 to 15 parts by weight, particularly preferably from 1 to 10 parts by weight, and most preferably from 3 to 8 parts by weight, based on 100 parts by weight of the amine.

The reaction temperature can preferably be selected from, for example, but is not limited to, greater than or equal to 100° C., more preferably 100 to 300° C. particularly preferably 120 to 220° C., and most preferably 140 to 200° C. If the reaction temperature is too low, the reaction rate might be reduced too much. If the reaction temperature is too high, the risk of unwanted side reaction significantly reducing yield and/or selectivity will increase.

The reaction time depends on other reaction conditions and can be determined in orienting experiments. The reaction time is preferably less than or equal to 24 hours, more preferably less than or equal to 15 hours; further more preferably less than or equal to 10 hours, particularly preferably from 2 to 10 hours, and most preferably from 3 to 8 hours.

The reaction pressure is the autogenous pressure developing at the chosen reaction temperature. Alternatively, the reaction pressure can also be modified by adding a gas inert under the reaction conditions, which can be selected from, but is not limited to, a nitrogen gas, a noble gas, carbon dioxide, or mixtures of the aforesaid gases. The reaction pressure can preferably be selected from, for example, but is not limited to, 1 to 50 atm, more preferably 1 to 30 atm, and most preferably 5 to 25 atm.

In the present invention, the catalyst can be employed in fixed bed, fluidized bed or slurry reactor.

The reaction can be carried out continuously, semi-continuously or batch-wise. The order of the addition of the raw materials and/or of the catalyst to the reactor is not critical, and the best way and/or most advantageous order to add the material and catalyst can be determined in orienting experiments. Furthermore, the ammonia formed during the reaction can be removed from the reactor by appropriate means continuously or intermittently to shift the reaction equilibrium to the product side.

Appropriate reactors can preferably be selected from, for example, but are not limited to, stirred reactors and tubular reactors. The tubular reactors can preferably be selected from, for example, but are not limited to, tubular reactors with or without inserts, tubular reactors with or without mixing elements, tubular reactors with or without redispersing elements, tubular reactors with a combination of two or more members of the group including inserts, mixing elements and redispersing elements.

In the reaction process, the starting materials, intermediates, solvents and/or catalysts can be recovered and/or recycled to any appropriate step of the reaction process.

After the reaction is finished, the reaction product can be removed from the reactor. The process of work-up and/or product isolation can be achieved by means of any appropriate technique/means/process step. The appropriate technique/means/process step can be selected from, but is not limited to, distillation, crystallization, filtration, sedimentation, decantation, centrifugation, extraction, membrane separation, or other means, or a combination of two or more of the aforesaid techniques/means.

In the process of the reaction or after the reaction is finished, the catalyst can be recovered and/or recycled by means of any appropriate technique/means/process step. The appropriate technique/means/process step can preferably be selected from, for example, but is not limited to, distillation, crystallization, filtration, sedimentation, decantation, centrifugation, extraction, membrane separation, or other means or by a combination of two or more of the aforesaid techniques/means.

The catalyst can be recycled either without any further treatment or after an appropriate reconditioning or treatment step, including, but not limited to, separating the catalyst, washing the catalyst thoroughly with an appropriate solvent, drying, or a combination of two or more of the aforesaid techniques/means. Drying can be performed in virtue of various manners such as, for example, but not limited to, vacuum drying, microwave drying, ultrasonic drying, supercritical fluid drying or a combination of two or more of the aforesaid techniques/means.

EXAMPLES

The synthesis reactions were carried out in a stainless steel autoclave with inner volume of 100 cm$^3$. The starting materials and catalyst were charged into the reactor. By flushing the reactor with N$_2$, the air in the autoclave was replaced. Thereafter, the reactor was heated to the desired temperature for a defined period of time as indicated in the examples. At the end of the reaction, the resultant products were analyzed either by gas chromatography (GC) or by liquid chromatography (LC), depending on the choice of the starting material, the identification of the products was performed by "liquid chromatography-mass spectrometry" (LC-MS). Yields of products were calculated based on the weight of aromatic amine used.

Preparation of Catalyst

Example 1

$V_2O_5$ of analytically pure grade was used as a catalyst support. Phase composition of the $V_2O_5$ was confirmed by XRD (X-Ray Diffraction). The BET surface area of the $V_2O_5$ was about 40 m$^2$/g, and the pore volume of the $V_2O_5$ was 0.4 cm$^3$/g.

The catalyst was prepared by impregnating $V_2O_5$ into a solution containing 5 wt % $H_3PW_{12}O_{40}$. The volume of the impregnation solution corresponded to the volume of the $V_2O_5$. After being impregnated for 4 hours, the resultant catalyst precursor was dried at 120° C. for 12 hours in air atmosphere. After drying, the catalyst precursor was calcinated at 450° C. for 4 hours. The resulting catalyst was named catalyst A.

Example 2

$V_2O_5$ of analytically pure grade was used as a catalyst support. Phase composition of the $V_2O_5$ was confirmed by XRD. The BET surface area of the $V_2O_5$ was about 40 $m^2/g$, and the pore volume of the $V_2O_5$ was 0.4 $cm^3/g$.

The catalyst was prepared by impregnating $V_2O_5$ into a solution containing 1 wt % $H_3PW_{12}O_{40}$. The volume of the impregnation solution corresponded to the volume of the $V_2O_5$. After being impregnated for 4 hours, the resultant catalyst precursor was dried at 120° C. for 12 hours in air atmosphere, and then calcinated at 450° C. for 4 hours. The resulting catalyst was named catalyst B.

Example 3

$V_2O_5$ of analytically pure grade was used as a catalyst support. Phase composition of the $V_2O_5$ was confirmed by XRD. The BET surface area of the $V_2O_5$ was about 40 $m^2/g$, and the pore volume of the $V_2O_5$ was 0.4 $cm^3/g$.

The catalyst was prepared by impregnating $V_2O_5$ into a solution containing 5 wt % $H_3PW_{12}O_{40}$. The volume of the impregnation solution corresponded to the volume of the $V_2O_5$. After being impregnated for 4 hours, the resultant catalyst precursor was dried at 120° C. for 12 hours in air atmosphere. The dried catalyst precursor was then calcinated at 450° C. for 4 hours. The resulting catalyst was named catalyst C.

Example 4

$V_2O_5$ of analytically pure grade was used as a catalyst support. Phase composition of the $V_2O_5$ was confirmed by XRD. The BET surface area of the $V_2O_5$ was about 40 $m^2/g$, and the pore volume of the $V_2O_5$ was 0.4 $cm^3/g$.

The catalyst was prepared by impregnating $V_2O_5$ into a solution containing 5 wt % $H_3PW_{12}O_{40}$. The volume of the impregnation solution corresponded to the volume of the $V_2O_5$. After being impregnated for 4 hours, the resultant catalyst precursor was dried at 120° C. for 12 hours in air atmosphere, thereafter, calcined at 250° C. for 4 hours. The resulting catalyst was named catalyst D.

Example 5

$V_2O_5$ of analytically pure grade was used as a catalyst support. Phase composition of the $V_2O_5$ was confirmed by XRD. The BET surface area of the $V_2O_5$ was about 40 $m^2/$, and the pore volume of the $V_2O_5$ was 0.4 $cm^3/g$.

The catalyst was prepared by impregnating $V_2O_5$ into a solution containing 5 wt % $H_3PW_{12}O_{40}$. The volume of the impregnation solution corresponded to the volume of the $V_2O_5$. After being impregnated for 4 hours, the resultant catalyst precursor was dried at 120° C. for 12 hours in air atmosphere, and thereafter, calcinated at 650° C. for 4 hours. The resulting catalyst was named catalyst E.

Example 6

$V_2O_5$ of analytically pure grade was used as a catalyst support. Phase composition or the $V_2O_5$ was confirmed by XRD. The BET surface area of the $V_2O_5$ was about 40 $m^2/g$, and the pore volume of the $V_2O_5$ was 0.4 $cm^3/g$.

The catalyst was prepared by impregnating $V_2O_5$ into a solution containing 5 wt % $H_3PW_{12}O_{40}$. The volume of the impregnation solution corresponded to the volume of the $V_2O_5$. After being impregnated for 4 hours, the obtained catalyst precursor was dried at 120° C. for 12 hours in air atmosphere, thereafter, calcinated at 450° C. for 2 hours. The resulting catalyst was named catalyst F.

Example 7

γ-Alumina of analytically pure grade was used as a catalyst support. Phase composition of the γ-Alumina was confirmed by XRD. The BET surface area of the γ-Alumina was about 230 $m^2/g$, and the pore volume of the γ-Alumina was 0.65 $cm^3/g$.

The catalyst was prepared by impregnating γ-Alumina into a solution containing 5 wt % $H_3PW_{12}O_{40}$. The volume of the impregnation solution corresponded to the volume of the γ-Alumina. After being impregnated for 4 hours, the resultant catalyst precursor was dried at 120° C. for 12 hours in air atmosphere, thereafter, calcinated at 450° C. for 2 hours. The resulting catalyst was named catalyst G.

Preparation of N-Substituted Carbamates (R'(NH—CO—OR)$_n$)

Example 8

9.50 g aniline, 60.00 g methyl carbamate, 16.25 g methanol (molar ratio of aniline, methyl carbamate and methanol was 1:8:5), and 0.60 g catalyst A (6.32 parts by weight, based on 100 parts by weight of aniline) were charged into the reactor.

The reaction was performed at 160° C. for 4 hours under autogenous pressure. The ammonia formed during the reaction was continuously removed from the reactor. After the completion of the reaction, the yield of O-methyl N-phenyl carbamate (MPC) was analyzed by gas chromatography. The aniline conversion, MPC selectivity and MPC yield were 91.8%, 88.3% and 81.1%, respectively.

Example 9

9.50 g aniline, 60.00 g methyl carbamate, 16.25 g methanol (molar ratio of aniline, methyl carbamate and methanol was 1:8:5), and 0.60 g catalyst B (6.32 parts by weight, based on 100 parts by weight of aniline) were charged into the reactor.

The reaction was performed at 160° C. for 4 hours under autogenous pressure. The ammonia formed during the reaction was continuously removed from the reactor. After the completion of the reaction, the yield of O-methyl N-phenyl carbamate (MPC) was analyzed by gas chromatography. The aniline conversion, MPC selectivity and MPC yield were 91.0%, 85.7% and 78.0%, respectively.

Example 10

9.50 g aniline, 60.00 g methyl carbamate, 16.25 g methanol (molar ratio of aniline, methyl carbamate and methanol was 1:8:5), and 0.60 g catalyst C (6.32 parts by weight, based on 100 parts by weight of aniline) were charged into the reactor.

The reaction was performed at 160° C. for 4 hours under autogenous pressure. The ammonia formed during the reaction was continuously removed from the reactor. After the completion of the reaction, the yield of O-methyl N-phenyl carbamate (MPC) was analyzed by gas chromatography. The aniline conversion, MPC selectivity and MPC yield were 90.3%, 86.9% and 78.5%, respectively.

Example 11

9.50 g aniline, 60.00 g methyl carbamate, 16.25 g methanol (molar ratio of aniline, methyl carbamate and methanol was 1:8:5), and 0.60 g catalyst D (6.32 parts by weight, based on 100 parts by weight of aniline) were charged into the reactor.

The reaction was performed at 160° C. for 4 hours under autogenous pressure. The ammonia formed during the reaction was continuously removed from the reactor. After the completion of the reaction, the yield of O-methyl N-phenyl carbamate (MPC) was analyzed by gas chromatography. The aniline conversion, MPC selectivity and MPC yield were 85.4%, 78.5% and 67.0%, respectively.

Example 12

9.50 g aniline, 60.00 g methyl carbamate, 16.25 g methanol (molar ratio of aniline, methyl carbamate and methanol was 1:8:5), and 0.60 g catalyst E (6.32 parts by weight, based on 100 parts by weight of aniline) were charged into the reactor.

The reaction was performed at 160° C. for 4 hours under autogenous pressure. The ammonia formed during the reaction was continuously removed from the reactor. After the completion of the reaction, the yield of O-methyl N-phenyl carbamate (MPC) was analyzed by gas chromatography. The aniline conversion, MPC selectivity and MPC yield were 82.5%, 81.5% and 67.1%, respectively.

Example 13

9.50 g aniline, 60.00 g methyl carbamate, 16.25 g methanol (molar ratio of aniline, methyl carbamate and methanol was 1:8:5), and 0.60 g catalyst F (6.32 parts by weight, based on 100 parts by weight of aniline) were charged into the reactor.

The reaction was performed at 160° C. for 4 hours under autogenous pressure. The ammonia formed during the reaction was continuously removed from the reactor. After the completion of the reaction, the yield of O-methyl N-phenyl carbamate (MPC) was analyzed by gas chromatography. The aniline conversion, MPC selectivity and MPC yield were 88.2%, 80.2% and 70.7%, respectively.

Example 14

9.50 g aniline, 60.00 g methyl carbamate, 16.25 g methanol (molar ratio of aniline, methyl carbamate and methanol was 1:8:5), and 0.60 g catalyst A (6.32 parts by weight, based on 100 parts by weight of aniline) were charged into the reactor.

The reaction was performed at 160° C. for 4 hours under autogenous pressure. The ammonia formed during the reaction was continuously removed from the reactor.

In order to check the reusability of the catalyst, the reaction step as described above was repeated five times. Therefore, after each run the catalyst A was separated from the reaction mixture by filtration, washed with methanol, dried at 120° C. for 12 hours and charged back into the reactor for the next run.

After completion of the 5 repeated runs, the yield of O-methyl N-phenyl carbamate (MPC) was analyzed by gas chromatography. The aniline conversion, MPC selectivity and MPC yield were 88.5%, 82.7% and 73.2%, respectively.

Example 15

9.50 g aniline, 60.00 g methyl carbamate, 16.25 g methanol (molar ratio of aniline, methyl carbamate and methanol was 1:8:5), and 0.30 g catalyst A (3.16 parts by weight, based on 100 parts by weight of aniline) were charged into the reactor.

The reaction was performed at 160° C. for 4 hours under autogenous pressure. The ammonia formed during the reaction was continuously removed from the reactor. After the completion of the reaction, the yield of O-methyl N-phenyl carbamate (MPC) was analyzed by gas chromatography. The aniline conversion, MPC selectivity and MPC yield were 85.7%, 82.4% and 70.6%, respectively.

Example 16

9.50 g aniline, 60.00 g methyl carbamate, 16.25 g methanol (molar ratio of aniline, methyl carbamate and methanol was 1:8:5), and 0.90 g catalyst A (9.48 parts by weight, based on 100 parts by weight of aniline) were charged into the reactor.

The reaction was performed at 160° C. for 4 hours under autogenous pressure. The ammonia formed during the reaction was continuously removed from the reactor. After the completion of the reaction, the yield of O-methyl N-phenyl carbamate (MPC) was analyzed by gas chromatography. The aniline conversion, MPC selectivity and MPC yield were 92.3%, 89.1% and 82.2%, respectively.

Example 17

9.50 g aniline, 60.00 g methyl carbamate, 16.25 g methanol (molar ratio of aniline, methyl carbamate and methanol was 1:8:5), and 0.60 g catalyst A (6.32 parts by weight, based on 100 parts by weight of aniline) were charged into the reactor.

The reaction was performed at 140° C. for 4 hours under autogenous pressure. The ammonia formed during the reaction was continuously removed from the reactor. After the completion of the reaction, the yield of O-methyl N-phenyl carbamate (MPC) was analyzed by gas chromatography. The aniline conversion, MPC selectivity and MPC yield were 60.1%, 72.4% and 43.5%, respectively.

Example 18

9.50 g aniline, 60.00 g methyl carbamate, 16.25 g methanol (molar ratio of aniline, methyl carbamate and methanol was 1:8:5), and 0.60 g catalyst A (6.32 parts by weight, based on 100 parts by weight of aniline) were charged into the reactor.

The reaction was performed at 180° C. for 4 hours under autogenous pressure. The ammonia formed during the reaction was continuously removed from the reactor. After the completion of the reaction, the yield of O-methyl N-phenyl carbamate (MPC) was analyzed by gas chromatography. The aniline conversion, MPC selectivity and MPC yield were 83.8%, 77.3% and 64.8%, respectively.

Example 19

9.50 g aniline, 60.00 g methyl carbamate, 16.25 g methanol (molar ratio of aniline, methyl carbamate and methanol was 1:8:5), and 0.60 g catalyst A (6.32 parts by weight, based on 100 parts by weight of aniline) were charged into the reactor.

The reaction was performed at 160° C. for 2 hours under autogenous pressure. The ammonia formed during the reaction was continuously removed from the reactor. After the completion of the reaction, the yield of O-methyl N-phenyl carbamate (MPC) was analyzed by gas chromatography. The aniline conversion, MPC selectivity and MPC yield were 80.6%, 78.5% and 63.3%, respectively.

Example 20

9.50 g aniline, 60.00 g methyl carbamate, 16.25 g methanol (molar ratio of aniline, methyl carbamate and methanol was 1:8:5), and 0.60 g catalyst A (6.32 parts by weight, based on 100 parts by weight of aniline) were charged into the reactor.

The reaction was performed at 160° C. for 6 hours under autogenous pressure. The ammonia formed during the reaction was continuously removed from the reactor. After the completion of the reaction, the yield of O-methyl N-phenyl carbamate (MPC) was analyzed by gas chromatography. The aniline conversion, MPC selectivity and MPC yield were 92.5%, 85.4% and 79.0%, respectively.

Example 21

9.50 g aniline, 60.00 g methyl carbamate, 3.25 g methanol (molar ratio of aniline, methyl carbamate and methanol was 1:8:1), and 0.60 g catalyst A (6.32 parts by weight, based on 100 parts by weight of aniline) were charged into the reactor.

The reaction was performed at 160° C. for 4 hours under autogenous pressure. The ammonia formed during the reaction was continuously removed from the reactor. After the completion of the reaction, the yield of O-methyl N-phenyl carbamate (MPC) was analyzed by gas chromatography. The aniline conversion, MPC selectivity and MPG yield were 95.3%, 83.6% and 79.7%, respectively.

Example 22

9.50 g aniline, 60.00 g methyl carbamate, 32.50 g methanol (molar ratio of aniline, methyl carbamate and methanol was 1:8:10), and 0.60 g catalyst A (6.32 parts by weight, based on 100 parts by weight of aniline) were charged into the reactor.

The reaction was performed at 160° C. for 4 hours under autogenous pressure. The ammonia formed during the reaction was continuously removed from the reactor. After the completion of the reaction, the yield of O-methyl N-phenyl carbamate (MPC) was analyzed by gas chromatography. The aniline conversion, MPC selectivity and MPC yield were 82.4%, 92.4% and 76.1%, respectively.

Example 23

9.50 g aniline, 15.00 g methyl carbamate, 16.25 g methanol (molar ratio of aniline, methyl carbamate and methanol was 1:2:5), and 0.60 g catalyst A (6.32 parts by weight, based on 100 parts by weight of aniline) were charged into the reactor.

The reaction was performed at 160° C. for 4 hours under autogenous pressure. The ammonia formed during the reaction was continuously removed from the reactor. After the completion of the reaction, the yield of O-methyl N-phenyl carbamate (MPC) was analyzed by gas chromatography. The aniline conversion, MPC selectivity and MPC yield were 66.5%, 70.8% and 47.1%, respectively.

Example 24

9.50 g aniline, 75.00 g methyl carbamate, 16.25 g methanol (molar ratio of aniline, methyl carbamate and methanol was 1:10:5), and 0.60 g catalyst A (6.32 parts by weight, based on 100 parts by weight of aniline) were charged into the reactor.

The reaction was performed at 160° C. for 4 hours under autogenous pressure. The ammonia formed during the reaction was continuously removed from the reactor. After the completion of the reaction, the yield of O-methyl N-phenyl carbamate (MPC) was analyzed by gas chromatography. The aniline conversion, MPC selectivity and MPC yield were 92.6%, 89.1% and 82.5%, respectively.

Example 25

9.50 g aniline, 71.27 g ethyl carbamate, 23.04 g ethanol (molar ratio of aniline, ethyl carbamate and ethanol was 1:8: 5), and 0.60 g catalyst A (6.32 parts by weight, based on 100 parts by weight of aniline) were charged into the reactor.

The reaction was performed at 160° C. for 4 hours under autogenous pressure. The ammonia formed during the reaction was continuously removed from the reactor. After the completion of the reaction, the yield of O-ethyl N-phenyl carbamate (EPC) was analyzed by gas chromatography. The aniline conversion, EPC selectivity and EPC yield were 82.6%, 79.3% and 65.5%, respectively.

Example 26

9.50 g aniline, 93.72 g n-butyl carbamate, 37.06 g n-butanol (molar ratio of aniline, n-butyl carbamate and n-butanol was 1:8:5), and 0.60 g catalyst A (6.32 parts by weight, based on 100 parts by weight of aniline) were charged into the reactor.

The reaction was performed at 160° C. for 4 hours under autogenous pressure. The ammonia formed during the reaction was continuously removed from the reactor. After the completion of the reaction, the yield of O-n-butyl N-phenyl carbamate (BPC) was analyzed by gas chromatography. The aniline conversion, BPC selectivity and BPC yield were 50.1%, 75.0% and 37.6%, respectively.

Example 27

12.22 g 2,4-toluene diamine, 60.00 g methyl carbamate, 16.25 g methanol (molar ratio of 2,4-toluene diamine, methyl carbamate and methanol was 1:8:5), and 0.60 g catalyst A (6.32 parts by weight, based on 100 parts by weight of aniline) were charged into the reactor.

The reaction was performed at 160° C. for 4 hours under autogenous pressure. The ammonia formed during the reaction was continuously removed from the reactor. After the completion of the reaction, the yield of corresponding biscarbamate was analyzed by gas chromatography. The toluene diamine conversion, selectivity and yield of the corresponding biscarbamate were 40.1%, 76.6% and 30.7%, respectively.

Example 28

9.50 g aniline, 60.00 g methyl carbamate, 16.25 g methanol (molar ratio of aniline, methyl carbamate and methanol was 1:8:5), and 0.60 g catalyst G (6.32 parts by weight, based on 100 parts by weight of aniline) were charged into the reactor.

The reaction was performed at 160° C. for 4 hours under autogenous pressure. The ammonia formed during the reaction was continuously removed from the reactor. After the completion of the reaction, the yield of O-methyl N-phenyl carbamate (MPC) was analyzed by gas chromatography. The aniline conversion, MPC selectivity and MPC yield were 74.3%, 72.5% and 53.9%, respectively.

Although the present invention is illustrated through Examples, it is not limited by these Examples in any way. Without departing from the spirit and scope of this invention, those skilled in the art can make any modifications and alternatives. And the protection of this invention is based on the scope defined by the claims of this application.

What is claimed is:

1. A method for preparing a N-substituted carbamate, comprising
  (1) reacting
    (a) one or more N-unsubstituted carbamates, with
    (b) one or more amines selected from primary amines and secondary amines, in the presence of (c) a catalyst in which the active component comprises a heteropoly acid and the component of the catalyst support comprises a metal oxide or a metalloid oxide, thereby forming the N-substituted carbamate wherein the catalyst support component comprising a metal oxide or a metalloid oxide is selected from the group consisting of zirconium oxide, titanium oxide, zinc oxide, silicon oxide, magnesium oxide, calcium oxide, tin oxide, barium oxide, cerium oxide, lanthanum oxide, vanadium pentoxide, aluminium oxide and mixtures thereof.

2. The method of claim 1, wherein the heteropoly acid is a Keggin type heteropoly acid.

3. The method of claim 2, wherein the heteropoly acid is selected from the group consisting of $H_3PW_{12}O_{40} \cdot nH_2O$, $H_3PMo_{12}O_{40} \cdot nH_2O$, $H_4SiW_{12}O_{40} \cdot nH_2O$ and $H_4SiMo_{12}O_{40} \cdot nH_2O$.

4. The method of claim 3, wherein the metal oxide is selected from the group consisting of a vanadium pentoxide, an aluminium oxide and mixtures thereof.

5. The method of claim 1, wherein the load of the active component of the catalyst is from 0.1 to 20 wt. %, based on 100 wt. % of the catalyst support.

6. The method of claim 1, wherein the amount of the catalyst is less than or equal to 20 parts by weight, based on 100 parts by weight of the amount of said amine component.

7. The method of claim 6, wherein the amount of the catalyst is from 0.1 to 15 parts by weight, based on 100 parts by weight of the amount of said amine component.

8. The method of claim 7, wherein the amount of the catalyst is from 3 to 8 parts by weight, based on 100 parts by weight of the amount of said amine component.

9. The method of claim 1, wherein the mol ratio of the amino group of said amine component to said carbamate is from 1:1 to 1:30.

10. The method of claim 1, wherein the reaction temperature of said reaction for preparing the N-substituted carbamate is greater than or equal to 100° C.

11. The method of claim 10, wherein the reaction temperature of said reaction for preparing the N-substituted carbamate is from 140 to 200° C.

\* \* \* \* \*